United States Patent
Stahl et al.

(10) Patent No.: US 10,126,709 B2
(45) Date of Patent: Nov. 13, 2018

(54) APPARATUS AND METHOD FOR PERFORMING IN-LINE LENS-FREE DIGITAL HOLOGRAPHY OF AN OBJECT

(71) Applicant: IMEC VZW, Leuven (BE)

(72) Inventors: Richard Stahl, Rotselaar (BE); Murali Jayapala, Boutersem (BE); Andy Lambrechts, Herent (BE); Geert Vanmeerbeeck, Keerbergen (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 15/727,832

(22) Filed: Oct. 9, 2017

(65) Prior Publication Data

US 2018/0046139 A1    Feb. 15, 2018

Related U.S. Application Data

(63) Continuation-in-part of application No. 15/039,549, filed as application No. PCT/EP2014/076270 on Dec. 2, 2014, now Pat. No. 9,811,051.

(30) Foreign Application Priority Data

Dec. 2, 2013   (EP) .................................... 13195248

(51) Int. Cl.
    *G03H 1/04*   (2006.01)
    *G03H 1/26*   (2006.01)
    (Continued)

(52) U.S. Cl.
    CPC ....... *G03H 1/0443* (2013.01); *G01N 15/1404* (2013.01); *G01N 15/147* (2013.01);
    (Continued)

(58) Field of Classification Search
    CPC ................ G01J 3/2823; G03H 1/0443; G03H 2001/0452; G01N 15/14; G01N 15/1404; G01N 15/1434
    See application file for complete search history.

(56) References Cited

U.S. PATENT DOCUMENTS

6,411,406 B1    6/2002 Kreuzer
8,314,933 B2 *  11/2012 Cui .................... G01N 21/6458
                                                         356/436
(Continued)

FOREIGN PATENT DOCUMENTS

WO    2012/150472 A1    11/2012

OTHER PUBLICATIONS

Fienup, J.R., "Reconstruction of an Object From the Modulus of its Fourier Transform", Optics Letters, vol. 3, No. 1, Jul. 1978, pp. 27-29.

(Continued)

*Primary Examiner* — Jonathan Hansen
(74) *Attorney, Agent, or Firm* — McDonnell Boehnen Hulbert & Berghoff LLP

(57) ABSTRACT

Embodiments described herein relate to lens-free imaging. One example embodiment may include a lens-free imaging device for imaging a moving sample. The lens-free imaging device may include a radiation source configured to emit a set of at least two different wavelengths towards the moving sample. The lens-free imaging device is configured to image samples for which a spectral response does not substantially vary for a set of at least two different wavelengths. The lens-free imaging device may also include a line scanner configured to obtain a line scan per wavelength emitted by the radiation source and reflected by, scattered by, or transmitted through the moving sample. The line scanner is configured to regularly obtain a line scan per wavelength.

(Continued)

Either the radiation source or the line scanner is configured to isolate data of the at least two different wavelengths.

20 Claims, 7 Drawing Sheets

(51) Int. Cl.
*G01N 15/14* (2006.01)
*G01N 15/10* (2006.01)

(52) U.S. Cl.
CPC ..... *G01N 15/1429* (2013.01); *G01N 15/1434* (2013.01); *G03H 1/0465* (2013.01); *G03H 1/2645* (2013.01); *G01N 2015/1006* (2013.01); *G01N 2015/1454* (2013.01); *G01N 2015/1472* (2013.01); *G01N 2015/1486* (2013.01); *G03H 2001/0447* (2013.01); *G03H 2001/0452* (2013.01); *G03H 2001/266* (2013.01); *G03H 2210/62* (2013.01); *G03H 2222/16* (2013.01)

(56) References Cited

U.S. PATENT DOCUMENTS

| | | |
|---|---|---|
| 2010/0253986 A1 | 10/2010 | Awatsuji et al. |
| 2011/0292402 A1 | 12/2011 | Awatsuji et al. |
| 2012/0122084 A1* | 5/2012 | Wagner ............... C12N 5/0612 435/6.1 |
| 2012/0225475 A1* | 9/2012 | Wagner ............... G01N 15/14 435/288.7 |
| 2014/0376816 A1* | 12/2014 | Lagae ............... G01N 15/1436 382/195 |
| 2015/0276589 A1* | 10/2015 | Wagner ............... G01N 21/39 356/440 |

OTHER PUBLICATIONS

Fienup, J.R.,"Phase Retrieval Algorithms: A Comparison", Applied Optics, vol. 21, No. 15, Aug. 1, 1982, pp. 2758-2769.
Awatsuji, Yasuhiro et al., "Single-Shot Phase-Shifting Color Digital Holography", Lasers and Electro-Optics Society, The 20th Annual Meeting of the IEEE, Oct. 1, 2007, pp. 84-85.
Kakue, Takashi et al., "Parallel Phase-Shifting Color Digital Holography Using Two Phase Shifts", Appiled Optics, vol. 48, No. 34, Dec. 1, 2009, pp. H244-H250.
Garcia-Sucerquia, Jorge, "Color Lensless Digital Holographic Microscopy With Micrometer Resolution", Optics Letters, vol. 37, No. 10, May 15, 2012, pp. 1724-1726.
Greenbaum, Alon et al., "Wide-Field Computational Color Imaging Using Pixel Super-Resolved On-Chip Microscopy", Optics Express, vol. 21, No. 10, May 14, 2013, pp. 12469-12483.
European Search Report, European Patent Application No. 13195248. 3, dated Apr. 24, 2014, 11 pages.
PCT Search Report and Written Opinion, PCT International Application No. PCT/EP2014/076270, dated Feb. 9, 2015, 16 pages.
Gorocs, Zoltan et al., "In-Line Color Digital Holographic Microscope for Water Quality Measurements", Laser Applications in Life Sciences, SPIE, vol. 7376, No. 1, Jun. 25, 2010, pp. 1-10.

* cited by examiner

APPARATUS AND METHOD FOR PERFORMING IN-LINE LENS-FREE DIGITAL HOLOGRAPHY OF AN OBJECT

CROSS-REFERENCE TO RELATED APPLICATIONS

The present application is a continuation-in-part (CIP) application claiming priority to U.S. patent application Ser. No. 15/039,549. U.S. patent application Ser. No. 15/039,549 is a national stage entry of PCT/EP2014/076270 filed Dec. 2, 2014, which claims priority to European Patent Application No. 13195248.3 filed on Dec. 2, 2013. The contents of each of the priority documents are hereby incorporated by reference.

FIELD OF THE DISCLOSURE

The present disclosure relates to an apparatus and method for performing lens-free digital holography of an object.

BACKGROUND

Gabor invented holography in 1948. It involves irradiating an object with a radiation beam of strong coherence. The waves which are scattered by the object interfere with the background wave on a photographic film or digital image sensor, where interference patterns are recorded. Based on the recorded interference pattern it is possible to reconstruct the original object wave field.

Since digital image sensors (camera sensors organized into semiconductor matrix based for instance on CCD, CMOS and similar configurations), digital holography has gained grounds. Holograms exposed on conventional photo materials need to be treated physically or chemically. This need is removed in the field of digital holograms. Moreover, the recorded hologram information can be stored in digital memory. The stored hologram can also be improved by appropriate software algorithms on the basis of the digital information only. The spatial image can for instance also be reconstructed from the hologram in a numerical way; there is no need for an illuminating light source and other optical means for the reconstruction of the spatial image.

Lens-free imaging is a microscopic imaging method based on the principal of in-line holography. In-line holography is a commonly used holographic imaging technique, and is known because of its simplicity and minimal optical hardware requirements. The in-line holography technique however suffers from the so-called twin-image problem, being the inherent artifact of out-of-focus virtual object information appearing in the in-focus real object image. Some techniques can eliminate the twin-image artifact. They can be categorized in two groups. A first group is constituted by support-/mask-based methods, which cannot be applied in complex object imaging as it is impossible to create a good mask for an object without obscuring the object right next to it. The other group is constituted of mask less iterative phase retrieval methods, which rely on acquisition of multiple images with varying information content. These multiple images with varying information content can be acquired by varying the phase, the imaging distance or the illumination wavelength between the different subsequent acquisitions. The multi-image acquisition can either performed in the time domain, for instance sequentially recording image after image, or in the space domain, for instance splitting up the light into multiple optical parts to vary the phase of light arriving at the sensor (at the pixel level) or to vary the optical path (at sensor level).

The multi-image acquisition performed in the time domain is not suitable for high speed imaging (e.g. in real-time video applications) as the acquisitions at different time-instances will typically record slightly or seriously different object perspectives (for instance objects rotating or shifting). The multi-image acquisition performed in the spatial domain, realized in the prior art for example using a beam splitter, has limited performance due to the fact that the imaging conditions cannot be optimized due to the presence of the extra optical hardware. For instance, a beam splitter does itself restrict the minimal distance from object to imager. This results in serious resolution degradation of the final reconstructed image.

Today, there exists a need for apparatuses and methods which are suitable for performing high-speed high resolution in-line lens-free digital imaging.

In WO2012/150472 an apparatus for producing three-dimensional color images is disclosed, the apparatus comprising at least two feeding light sources generating coherent light beams of different colors, at least two optical fibers having input ends and light emitting ends, the input ends of the optical fibers being connected to the feeding light sources, respectively, the light emitting ends of the optical fibers being placed closely side by side and constituting an illuminating light source, an object space suitable for locating an object to be illuminated by the illuminating light source, at least one digital image sensing device for recording an interference pattern of reference light beams and object light beams scattered on or reflected by the object as a hologram, and the digital image processing device for producing the three dimensional color images of the object from the hologram recorded by the at least one digital image sensing device with a correction of distortions resulting from placing side by side the light emitting ends of the optical fibers.

Here, a plurality of feeding light sources each emit light with a very narrow wavelength spectrum, from neighboring but still substantially different locations, such that a correction of distortions is necessary. Such a configuration puts stringent conditions on the light sources used, making it an expensive solution. Moreover, multiple sources are needed, which again increases the cost and results in relatively large devices. Also, at the digital image sensing device, wavelength filters with a relatively broad wavelength range are applied, in order to be able to extract information for different colors.

SUMMARY

It is an aim of the present disclosure to provide an apparatus for performing lens-free digital holography of an object which is suitable for performing high-speed high resolution holographic imaging.

This aim is achieved according to the disclosure with the apparatus showing the technical characteristics of the first independent claim.

It is another aim of the present disclosure to provide a method for performing in-line lens-free digital holography of an object.

This aim is achieved according to the disclosure with a method comprising the steps of the second independent claim.

In a first aspect of the present disclosure, an apparatus is disclosed for performing in-line lens-free digital holography of an object, comprising:

a single point light source adapted for emitting coherent light;

an image sensing device adapted and arranged for recording interference patterns resulting from interference from light waves directly originating from the point light source and object light waves, the object light waves originating from scattering or reflection of light waves from the point light source by the object, the image sensing device comprising a plurality of pixels;

wherein the image sensing device is adapted for receiving and recording, at the same moment in time, a plurality of interference patterns by a respective plurality of disjoint subsets of pixels.

The plurality of interference patterns may be suitable for retrieving or deriving phase information of the three-dimensional interference space, more specifically suitable for retrieving or deriving phase information of the object.

According to some embodiments, the object is a translucent object. For example, the object can be transparent. According to some embodiments the object can be more than 10% or more than 25%, or more than 50% or more than 60% or more than 70% or more than 80% or more than 90% or more than 95% or more than 99% translucent or transparent, which means that it would allow a respective percentage of the incoming light passing through it.

A single point light source is a light source of the point source type. Although the concept of a point source is in principle a mathematical concept, a light source of the point source type is meant to be any light source which approximates the mathematical concept to a very large extent, as will be recognized. It may for instance be a light source with an emission aperture of 1 micrometer to 100 micrometer. For example, the aperture size can be 1 micrometer, which would be considered "small". For example, the aperture size can be 50 micrometer, this would be considered "large".

According to some embodiments, the apparatus further comprises or relates to an object space suitable for locating the object and positioned in close proximity of the point light source, for subjecting the object to light waves of the point light source. The object can be positioned within the range of hundred or a few hundred (e.g. 200 or 300) of micrometers to a ten or a few tens (e.g. 20 or 30) of centimeters from the light source. For example, the object can be positioned at a distance of 1 millimeter from the light source.

The object space may be situated in between the point light source and the image sensing device. The object space may be situated along or within the light path of the light emitted from the point light source and the image sensing device.

According to some embodiments, the image sensing device is a digital image sensing device. The digital image sensing device may comprise a plurality of pixels. A pixel can comprise or consist of a photodiode and readout electronics.

According to some embodiments, the apparatus further comprises a processor adapted for deriving phase information by using at least the plurality of interference patterns, or based on the plurality of interference patterns, or based on the plurality of interference patterns only. Deriving or retrieving phase information based on the plurality of interference patterns may comprise an up-sampling step of the holographic images, to increase the resolution of the image. It has moreover been shown that the use of up-sampling methods which can be used to increase the resolution of each of the recorded interference patterns does not impact the convergence of typical iterative phase retrieval methods.

According to some embodiments, the pixels are arranged in a regularly spaced matrix pattern.

According to some embodiments, pixels of each subset of pixels are homogeneously distributed over a main planar surface of the image sensing device.

According to some embodiments, pixels of each subset of pixels are spaced from each other at constant distances, and wherein respective resulting grids are offset with respect to each other by constant distances.

For instance, in the case of two subsets of pixels, these can be organized in a chess board configuration.

According to some embodiments, the pixels of each disjoint subset are arranged in rows (or columns) of the regularly spaced matrix pattern.

According to some embodiments, the point light source comprises a broad wavelength spectrum light source and a pinhole structure, the broad wavelength spectrum light source being arranged such that it emits light towards a pinhole structure. In another view, the point light source (e.g., a broad wavelength spectrum light source) can be embodied as a light source behind, i.e. on a first side of, a pinhole in a plate or other light blocking means. The other side of the plate of light blocking means can host the object space and/or image sensing device.

According to some embodiments, the broad wavelength spectrum light source comprises a white laser device or a LED device.

According to some embodiments, the image sensing device comprises for each of the disjoint subsets of pixels, a respective narrow band wavelength filter positioned above each of the pixels of the disjoint subset of pixels, wherein a wavelength range of each narrow band wavelength filter falls within the broad wavelength spectrum of the point light source, and wherein these wavelength ranges of the narrow band wavelength filters are non-overlapping. In other words, for example, the passbands of different filters do not overlap. In practice, this may mean that the overlap is below a predetermined level. For a given application, a suitable degree of overlap may be determined. For instance, a first narrow band wavelength filter can be considered as overlapping with a second narrow band wavelength filter if there exists more than 90, or more than 95, or more than 98, or more than 99, or more than 99.9 percent overlap. In other words, a first narrow band wavelength filter can be considered as non-overlapping with a second narrow band wavelength filter if there exists less than 10, or less than 5, or less than 2, or less than 1, or less than 0.01 percent overlap.

According to some embodiments, the wavelength range of each narrow band filter is smaller than N nm, and wherein the broad wavelength spectrum has a wavelength range larger than N×M nm, M being the number of narrow band filter comprised or present in the apparatus.

For example, in case of four wavelength filters, the wavelength range of each narrow band filter can for instance be smaller than 5 nm (for instance within the range of 1 nm to 5 nm; smaller values are not excluded but may include light sources with relatively high intensity; the latter may be detrimental to certain objects, as for instance biological objects), and the broad wavelength spectrum can have a wavelength range larger than 20 nm (for instance the wavelength range can be within the range between 20 nm and 100 nm). In another example, the wavelength range of each narrow band filter of a set of ten non-overlapping narrow band wavelength filters can be smaller than 2 nm, and all of them can be fit in a 20 nm broad wavelength spectrum. More generally, the sum of the wavelength ranges of the respective set of narrow band filters may be smaller than the wavelength range of the broad wavelength spectrum. A broad wavelength spectrum may include a spectrum which is continuous and extends over a broad wavelength range. It is a characteristic of such broad wavelength spectrum that the light intensity within this broad range is never close to zero or zero, i.e. the intensity of the broad spectrum wavelength light source is always substantially different from zero, within this broad range. According to some embodiments, the broad wavelength spectrum has a Gaussian-type profile.

In a second aspect of the present disclosure, a method is disclosed for performing in-line lens-free digital holography of an object, comprising:
  emitting essentially coherent light from a single point light source;
  locating the object, for instance in an object space, positioned in close proximity of the point light source, and subjecting the object to light waves of the point light source;
  receiving and recording interference patterns resulting from interference from light waves directly originating from the point light source and object light waves, the object light waves originating from scattering or reflection of light waves from the point light source by the object, with an image sensing device comprising a plurality of pixels;
  wherein receiving and recording interference patterns comprises receiving and recording at the same moment in time a plurality of interference patterns by a respective plurality of disjoint subsets of pixels.

According to some embodiments, the method further comprises retrieving or deriving phase information of the object by performing an iterative phase retrieval algorithm, using the plurality of interference patterns, for instance performed on a processor. Iterative phase retrieval algorithms may be used. This field has been explored scientifically since the 1970s. See for instance J. R. Fienup, "Reconstruction of an object from the modulus of its Fourier transform", Optics Letters, Vol. 3, Issue 1, pp. 27-29 (1978) and J. R. Fienup, "Phase retrieval algorithms: a comparison", Applied Optics, Vol. 21, Issue 15, pp. 2758-2769 (1982).

According to some embodiments, the method further comprises emitting a broad wavelength spectrum of light with the point light source and filtering the incoming light for each of the pixels belonging to a same subset, with a respective narrow band wavelength filter, for each disjoint subset, before receiving the plurality of interference patterns by a plurality of disjoint subsets of pixels, wherein a wavelength range of each narrow band wavelength filter falls within the broad wavelength spectrum of light of the point light source, and wherein wavelength ranges of respective narrow band wavelength filters are non-overlapping.

A third aspect of the present disclosure, discloses the use of an apparatus according to any of the embodiments of the first aspect, for performing in-line lens-free digital holography of an object, by receiving and recording, at the same moment in time, a plurality of interference patterns by a respective plurality of disjoint subsets of pixels.

According to some embodiments, the object is a biological object, such as for instance a cell, a virus or a tissue.

A fourth aspect of the present disclosure, discloses a computer program product suitable for deriving phase information of an object based on a plurality of interference patterns received and recorded at the same moment in time by the apparatus according to any of the embodiments of the first aspect, when run on a computer.

In yet another aspect, embodiments described herein relate to a lens-free imaging device for imaging a moving sample, the lens-free imaging device comprising:
  a radiation source for emitting a set of at least two different wavelengths towards the moving sample, wherein the lens-free imaging device is suitable for imaging samples of which the spectral response is not substantially varying for the at least two different wavelengths within one set,
  a line scanner for obtaining a line scan per wavelength emitted by the radiation source and reflected by, scattered by and/or transmitted through the moving sample wherein the line scanner is adapted for regularly obtaining a line scan per wavelength,
  wherein either the radiation source or the line scanner is adapted for allowing isolating data of the at least two different wavelengths. The at least two different wavelengths may be at least three different wavelengths.

Where in embodiments reference is made to a radiation source or a line scanner being adapted for allowing isolating data of at least two different wavelengths, reference may be made to a configuration of the radiation source and/or a line scanner such that data of a first wavelength and data of at least a second wavelength can be captured such that the data of the first wavelength can be distinguished from the data of the second wavelength. The system may be adapted for acquiring data such that the data of the first wavelength and the data of the at least second wavelength can be acquired individually from each other.

In some embodiments, lens-free imaging devices for imaging a moving sample as well as a method for imaging a moving sample are provided.

The line scanner may comprise a line of scanning pixels for obtaining a line scan.

In some embodiments, a lens-free imaging device with which it is possible to do multi-wavelength imaging on a moving sample is provided. Lens-free imaging thereby may allow high precision mechanical components are not required and that a compact imaging device can be realized. Multi-wavelength imaging may provide enhanced resolution. In some embodiments, multi-wavelength imaging with a lens-free imaging device can be done on a moving sample (e.g. in flow). Multi-wavelength imaging on a moving sample is enabled because of the line scanner, which has a higher scanning speed some large field of view imaging systems. Line scanners according to the present disclosure only have detector lines comprising single lines of pixels and therefore are faster than two-dimensional sensors. Hence, lens-free imaging devices according to the present disclosure allow scanning of samples which are moving at a higher speed than would be possible in some large field of view imaging systems. Having a line scanner instead of a large field of view imaging system may allow an easier, and hence cheaper, control, moreover a line scanner is smaller and hence has a reduced silicon cost. In some embodiments, the spacing between the different wavelengths in a set is smaller than 20 nm, because at this this distance the spectral information of the sample caused by the difference in illumination wavelength is limited. Thus the different line scans can be used to increase the signal to noise ratio.

In some embodiments, the lens-free imaging device comprises a processor adapted for stitching the obtained line scans per wavelength, thus obtaining, for each wavelength, an image of the sample.

In some embodiments, the image of the sample can be reconstructed by stitching the obtained line scans. In some embodiments, an image per wavelength can be obtained. In some embodiments, by combining imaging of a moving sample together with line scan imaging, and by stitching the obtained line scans it is possible to image samples with large volumes.

In some embodiments, the processor is adapted for recombining the obtained images to get a combined image, e.g. an image with higher resolution.

In some embodiments, a multi-wavelength image has a higher resolution than an image with only one wavelength. In some embodiments, the resolution of the obtained image can be increased by applying multi-wavelength iterative phase retrieval. This is possible because the spacing between the wavelengths of the same set is limited, hence a similar image for the different wavelengths is obtained (not disturbed by a difference in spectral response of the sample).

In some embodiments, the processor is adapted for analyzing the combined image to count the number of particles in the sample.

In some embodiments, it is possible to do statistical analysis on a moving sample. In some embodiments, the signal to noise ratio of the obtained image is increased because of the use of a set of at least two different wavelengths which also results in an improved accuracy when counting the number of particles in a sample.

In some embodiments, the radiation source has a spectrum covering the set of different wavelengths, the line scanner comprising a filter per wavelength, each in front of a separate detector line of the line scanner.

In some embodiments, a radiation source with a spectrum covering the different wavelengths can be used as radiation source and that no individual radiation sources per wavelength are required. This is enabled by using a filter per wavelength before detecting the incoming radiation with the line scanner.

In some embodiments, the radiation source comprises at least two single wavelength illumination sources, positioned for only illuminating one corresponding detector line of the line scanner.

In some embodiments, panchromatic line scan detectors can be used. In some embodiments, a higher sensitivity can be obtained because the use of filters is avoided. In some embodiments, there is a larger availability of multi-narrowband sources, especially in the 600 nm-700 nm range.

In some embodiments, the radiation source is adapted for transmitting at least two sets of wavelengths wherein the spacing between the sets of wavelengths is larger than the spacing between wavelengths within a set and wherein either the radiation source or the line scanner is adapted for isolating the at least two different wavelengths within in each set.

In some embodiments, multi-wavelength imaging can be combined with multi-spectral imaging. The latter may allow to distinguish different particles in the flow.

In some embodiments, the lens-free imaging device comprises a microfluidic device adapted for carrying the sample flow such that the sample can be imaged by the radiation source and the line scanner, wherein, when the sample is flowing in the microfluidic device, the flow speed of the sample is smaller than or equal to the speed that can be imaged by the line scanner.

Some embodiments include a microfluidic device and that by putting a sample in this device the sample flow is correctly positioned for imaging the sample and that the speed of the sample flow is matched with the speed of the line scanner. In some embodiments, the associated microfluidics are of low complexity. In some embodiments, the integration of the whole lens-free imaging system is made easier.

In some embodiments, the lens-free imaging system may be configured for performing industrial inspection.

In another aspect, embodiments relate to a method for imaging a moving sample, the method comprising:
  emitting a set of at least two different wavelengths towards the moving sample wherein the spacing between the wavelengths is selected such that the spectral response of the sample is not varying for the different wavelengths within one set,
  regularly obtaining a line scan per wavelength emitted by the radiation source and reflected by, scattered by and/or transmitted through the moving sample wherein the speed of obtaining the line scan per wavelength allows to image the moving sample,
  stitching the obtained line scans per wavelength together thus obtaining an image per wavelength,
  recombining the obtained images to get a combined image of the sample.

In some embodiments, the speed of a moving sample should be so small that the translation of the object during the exposure time (i.e. the image capture time) is smaller than the size of one pixel in the detector. The image capture time is the integration time of the pixels of the line scan. Typically all the pixels may be reset and read out at the same moment in time, i.e. they work in a so called global shutter mode.

In some embodiments, the method comprises a step analyzing the obtained combined image of the sample thereby counting the number of particles in the combined image.

In a third aspect embodiments of the present disclosure relate to a diagnostic device for diagnosing a status of an object or a patient, the diagnostic device comprising:
  a lens-free imaging device, according to example embodiments, for determining a quality or quantity of particles in a flow of a sample of the object or patient, and
  an output device for providing an output of the lens-free imaging device on which a diagnosis can be based.

In some embodiments, the output device is adapted for outputting a number of cells in a blood flow. The cells in the blood flow may be any of e.g. white blood cells, red blood cells, and/or platelets.

In yet another aspect, the present disclosure relates to an industrial inspection device for inspecting objects, the industrial inspection device comprising a lens-free imaging device according to an embodiment of the first aspect for inspecting an object or a flow of objects, and an output device for providing an output of the lens-free imaging device for characterizing the object or flow of objects. Examples of such inspection may be inspection of food, inspection of liquids, inspection of bulk materials, e.g. passing on a conveyor belt, etc.

It will be clear that features of one aspect of the disclosure can be combined mutates mutandis with features of other aspects of the disclosure, thus also forming embodiments of the present disclosure.

Particular aspects are set out in the accompanying independent and dependent claims. Features from the dependent claims may be combined with features of the independent claims and with features of other dependent claims as appropriate and not merely as explicitly set out in the claims.

These and other aspects will be apparent from and elucidated with reference to the embodiment(s) described hereinafter.

BRIEF DESCRIPTION OF THE DRAWINGS

The disclosure will be further elucidated with reference to the following description and the appended figures.

DETAILED DESCRIPTION

Figure 1:
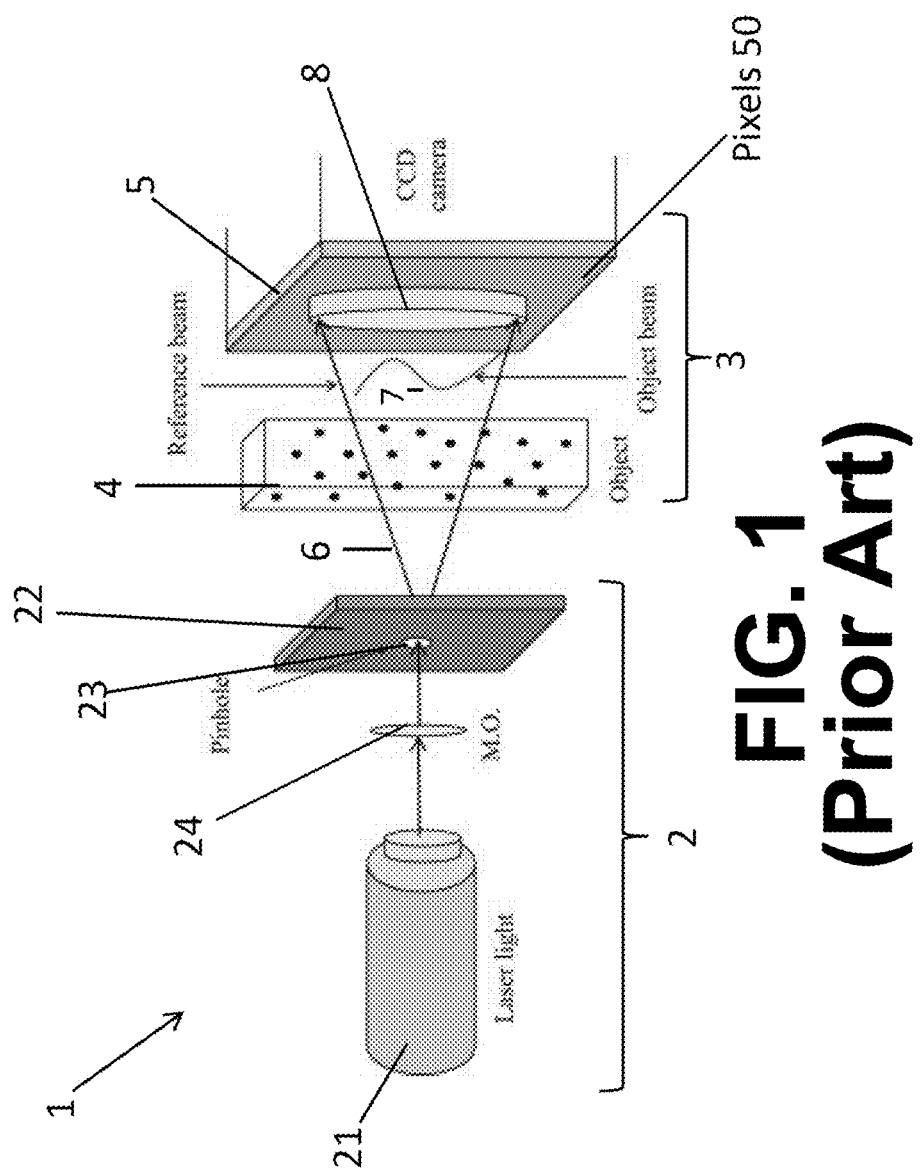
FIG. 1 shows a prior art setup of an in-line lens-free digital holography apparatus.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

Furthermore, the various embodiments, although referred to as "preferred" are to be construed as example manners in which the disclosure may be implemented rather than as limiting the scope of the disclosure.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present disclosure, the only enumerated components of the device are A and B, and further the claim should be interpreted as including equivalents of those components.

FIG. 1 illustrates a holographic apparatus 1 for performing in-line lens-free digital holography of an object, such as a translucent or transparent object. This apparatus 1 comprises a single point light source 2, being a light source of the point source type, adapted for emitting coherent or essentially coherent light. The single light source may be constituted of different components, and may comprise a plate 22 with a pinhole 23 positioned in front of a light source 21 as for instance a laser or LED light source. Between the light source 21 and the plate or light blocking means 22, optical components 24 may be provided such as for instance one or more lenses. Note that embodiments of the present disclosure are anyhow called "lens-free" as this does only refer to the fact that no optical components as for instance lenses are present or used on the side of the plate or light blocking means 22 opposite to the side where the laser or LED light source is located. The apparatus or system further comprises an object space 3 suitable for locating the object 4 and positioned in close proximity of the point light source 2, for subjecting the object 4 to light waves 6 of the point light source 2. The system or apparatus further comprises a digital image sensing device 5 adapted and arranged for recording two-dimensional interference patterns 8 within the three-dimensional interference space. The three-dimensional interference space is resulting from the interference of light waves 6 directly originating from the point source 2 and object light waves 7. This object light waves 7 originate from scattering and/or reflection of light waves emitted from the point light source 2 by the object 4. The digital image sensing device 5 typically comprises a plurality of pixels 50. A problem with some in-line lens-free digital holography setups, is that an inherent artifact of a twin image is created in the interference patterns 8, which are detected with the digital image sensing device 5.

According to aspects of the present disclosure, a similar holographic apparatus 1 is disclosed, wherein the digital image sensing device 5 is adapted for receiving and recording, at the same moment in time, a plurality of interference patterns 8 by a respective plurality of disjoint subsets of pixels. The plurality of interference patterns obtained as in embodiments of the present disclosure have been shown to be suitable for retrieving or deriving phase information of the three-dimensional interference space, especially phase information about the object. According to some embodiments the digital image sensing device further includes a processor adapted for deriving or retrieving the phase information based on, or at least on, the plurality of interference patterns 8 registered by the digital image sensing device 5.

Figure 2:
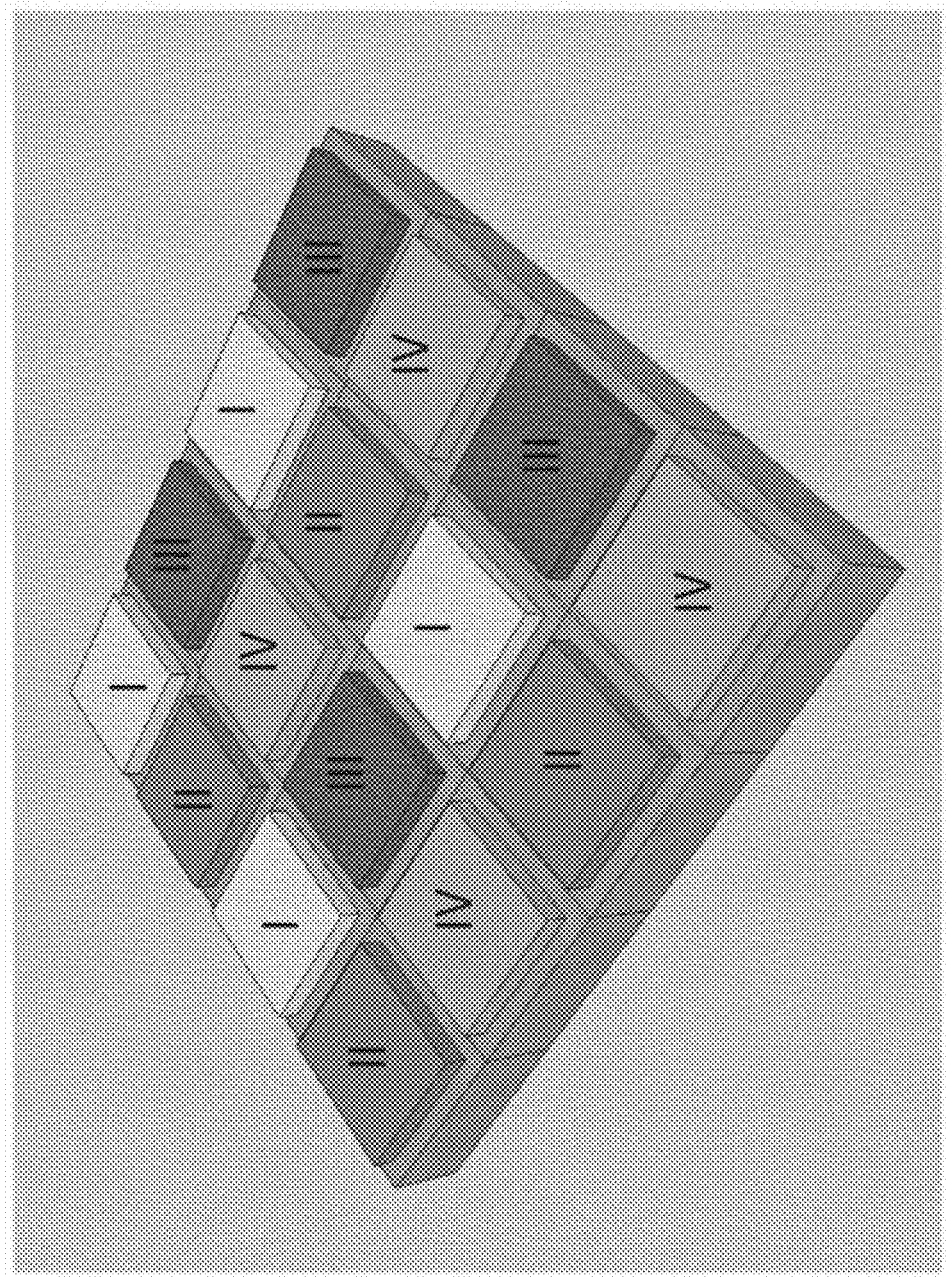
FIG. 2 is a perspective view, according to example embodiments.

FIG. 2 depicts an embodiment according to aspects of the present disclosure, wherein the digital image sensing device 5 comprises a plurality of pixels 50 which are arranged in a regular spaced matrix pattern. For example, the pixels of each subset of pixels may be homogeneously distributed over a main planar surface of the image sensing device 5. As pixels may be arranged in a regular matrix formation, the fact that the pixels of each subset of pixels are homogenously distributed over a main planar surface of the image sensing device, may imply that the pixels of each subset of pixels are spaced from each other at constant distances. The respective resulting grids, for each subset of pixels, are offset with respect of each other by constant distances.

For instance, in case the total amount of pixels 50 of the digital image sensing device 5 is divided in two subsets (I, II) of pixels which are equal in number, they can be distributed in a chess board formation. According to some embodiments, four subsets of pixels (I, II, III, IV) are formed which are equal in number of pixels, which are forming four-pixel squares. The four pixel positions of the four-pixel squares are represented by a pixel of each group of subset of pixels (I, II, III, IV) respectively. Such a four-pixel square formation may be repeated regularly and systematically along the main surface of the sensing device 5, for instance to thereby fill the complete main surface of the digital image sensing device 5.

According to some embodiments of the present disclosure, a variation in illumination wavelength is applied to acquire, in multiple holograms or interference patterns 8, slightly different information about the same object 4. This information is later recombined, for instance in an iterative phase retrieval algorithm, to suppress the twin image. In the state of the art, a multi-wavelength iterative phase retrieval method requires multiple holograms acquired with different illumination wavelengths. This is also the case in other multi-image correction methods. Aspects of the present disclosure are based on the idea of filtering the wavelengths only at the image sensing device or imager 5. This is after the moment that the photons of different wavelengths, originating from a broad wave-length spectrum light source, which is comprised in the point light source 2, have interfered with the object 4. This means that multiple photons with different wavelengths all interact with the object at the same time and this diffraction can be captured at a single moment, using a single digital image sensing device 5. According to some embodiments, a special designed image sensing device has been provided that can separate the different wavelengths and so the different interference patterns (or holograms). It is proposed to use multiple very narrow and possibly non-overlapping spectrum filters for different neighboring pixels of such a digital image sensing device 5. The filters can be pixel level integrated. This is depicted for instance in FIG. 2, wherein 4 by 4 pixels are disclosed of a digital image sensing device, wherein every 2 by 2 pixel sub array (four-pixel square) has four different narrowband filters (F1, F2, F3, F4) processed on top of its pixels. This imager can filter four different wavelengths and so four different hologram patterns from a single wideband coherent illumination 6 which interferes with the object light waves 7. These two by two subsets are repeated over the whole surface of the imager, creating a regular raster of pixels with individual wavelengths. In other words, the size of the four recorded holograms (recorded different wavelengths W1, W2, W3, W4) may be one fourth (½ in each dimension) of the size of the digital image sensing device 5. For example, the four by four image sensing device 5 in FIG. 1 is adapted for recording four holograms in a single shot: hologram 1 (2 by 2 pixels) at a wavelength W1 filtered out by filter F1, hologram 2 (2 by 2 pixels) at a wavelength W2 filtered out by filter F2, etc. An image interpolation technique can be used to up-sample the individual holograms H1 to H4 into full size (four times four) holograms H1' to H4'. These up-sampled holograms can then be used as an input for a multi wavelength iterative phase retrieval algorithm.

Figure 3:
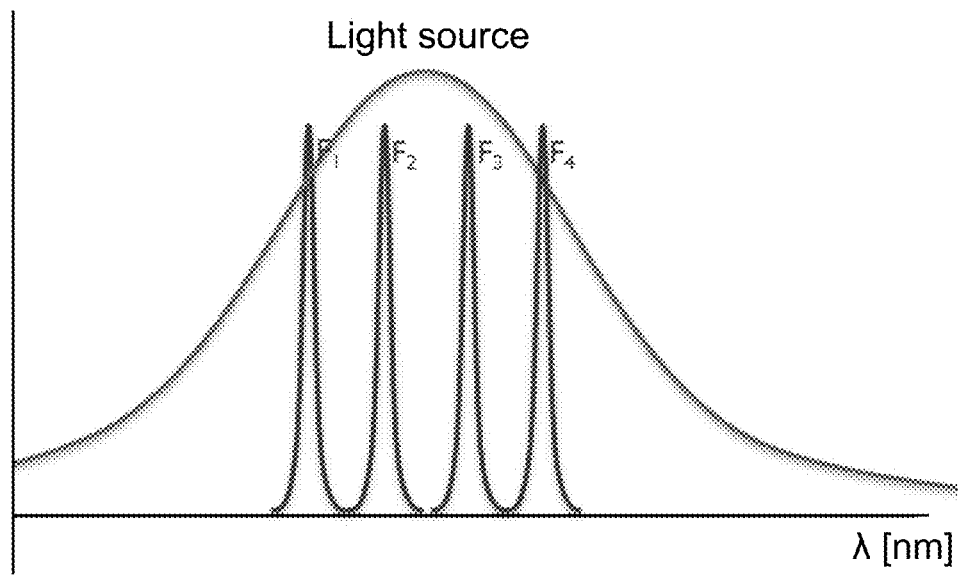
FIG. 3 is an illustration of the relative proportion and positioning of the broad band spectrum of the point light source and the narrow bands of the wavelength filters, according to example embodiments illustrated in FIG. 2.

The high-speed single shot lens-free imaging system may comprise a wideband coherent light source, as for instance an LED or for instance super-continuum laser as a wide laser. FIG. 3 illustrates the spectral characteristics of the wideband coherent light source (for instance an LED or a super-continuum laser) and the four corresponding narrowband filters F1 to F4 as described in relation to FIG. 2. Simulations and experiments have shown that there may be an approximately 30 to 40% degradation in final image resolution when comparing the "snapshots" four-wavelength reconstruction results with results based on a full sized single image reconstruction scenario. However the multi wavelength approach, according to some embodiments, can recover the phase information, which the state of the art single-image reconstruction cannot.

Figure 4:
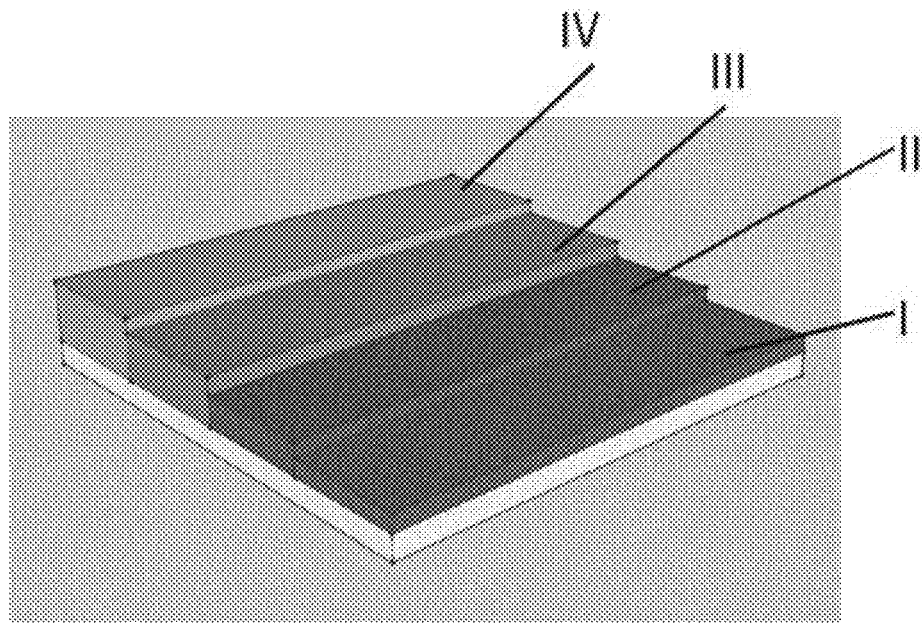
FIG. 4 is a perspective view, according to example embodiments.

According to a further embodiment of the line-scanner type, the filters can be spread across the image sensor in a staircase/wedge pattern, for instance as depicted in FIG. 4. Each filter can hereby cover a row of pixels of the image sensing device. This "wedge" architecture may be more suitable when there is a natural translation and movement in the object scene. Typical example is when objects are passed along a conveyer belt or roll along in between the imager with the filters on one side and the light source on the other side. In these embodiments, the pixels of each disjoint subset of pixels of the digital image sensing device are arranged in rows of the regularly spaced matrix pattern. Each filter area corresponds to a different narrowband region. Each filter area captures the part of the hologram corresponding to the specific wavelength of the filter. By scanning the object of interest, each filter area will capture the complete hologram at a specific wavelength. Once a scan or scanning movement is completed, holograms of different wavelengths are then used in a multi wavelength phase retrieval algorithm. Note that unlike in the previous embodiment, all the captured holograms are of the same resolution as the imager in one dimension (the other dimension is of arbitrary length as this is determined by the scan direction and length). This type of embodiment may achieve high-speed interference pattern recording by employing parallel multi wavelength imagers by exploiting the natural translation movement in such predetermined applications.

Figure 5:
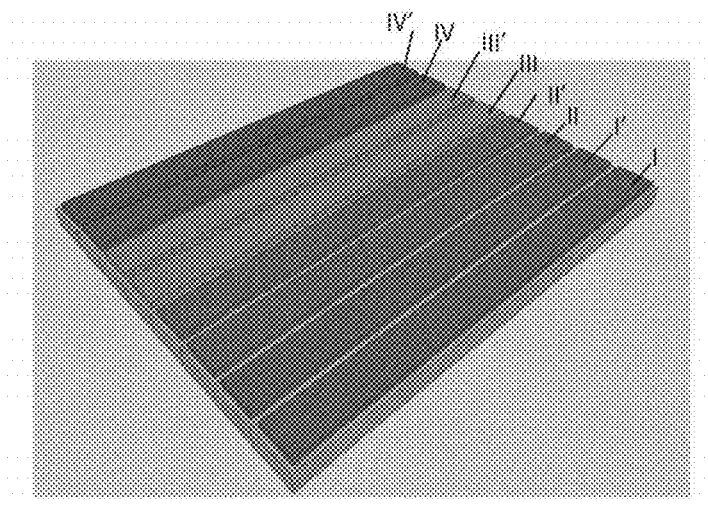
FIG. 5 is a perspective view, according to example embodiments.
Figure 6:
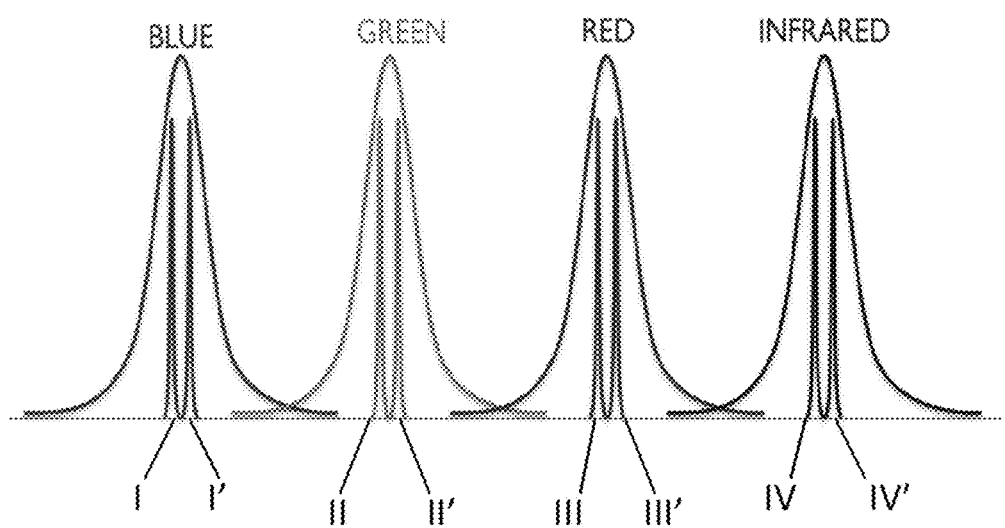
FIG. 6 is an illustration of the relative proportion and positioning of the broad band spectrum of the point light source and the narrow bands of the wavelength filters, according to example embodiments illustrated in FIG. 5.

In still another embodiment, also of the line-scanner type, as depicted for instance in FIG. 5, the filters (I, I', II, II', III, III', IV, IV') are spread across the image sensor as parallel stripes. They can be processed in sets of filters (for instance sets of two filters) per color. For instance, four color images, corresponding to different color-categories, as for instance Red (R), Green (G), Blue (B), Infrared (IR), can be generated while line-scanning (resulting from a relative translational movement between apparatus and object). Indeed, four sets of for instance two filters are provided (I, I'), (II, II'), (III, III'), (IV, IV'), the filters of each set belonging to the same color category. Images recorded with filters of the same color category then allow reduction or removal of the twin-image effect for image of the respective color category. This architecture may provide full color or multicolor lens-free imaging systems. Hereby the colors and thus respective filters can be chosen specifically based on a predetermined application. In this embodiment, two wavelengths are being used per color (to be able to use the iterative phase retrieval methods per color) and a total of four color categories, namely the blue, green, red and infrared color categories, enabling full color/four color lens-free line scanning. FIG. 6 illustrates the spectral characteristics of the full color (RGBI) line scanner described in relation with FIG. 5, comprising two narrowband spectral filters (I, I'), (II, II'), (III, III'), (IV, IV') per color (R,G,B,IR).

Embodiments described herein may provide several advantages. A single shot recording of multiple diffraction patterns (holograms) is possible, which enables iterative phase retrieval algorithms to be performed without incurring the previously described issues related to the retrieval of multiple diffraction patterns at different instances of time (time domain, vibration, object rotation, etc.), or at different locations (spatial domain; object too far). Some embodiments allow high-speed lens-free imaging. The acquisition speed equals the imager frame rate. Moreover, filter or delay structure can be chosen based on application. For instance the filter wavelengths can be chosen based on application. The point light source can be cheap, it can for instance be a LED light source, and does not necessarily have to be a laser or a plurality of lasers. Also, the use of a single source is sufficient for performing methods according to example embodiments. It has also been found that image reconstruction algorithms can be used, because of the setup.

Simulations have been made to illustrate the concept of aspects of the present disclosure. A simulation was first made of the outcome of the image sensor with the per-pixel filters on top in "snapshot" approach; i.e. wherein a plurality of interference patterns (here four) are received and recorded at the same moment in time, by a respective plurality of disjoint subsets of pixels. The simulation simulated the virtual result when using an image sensing device comprising for each of the four disjoint subsets of pixels, a respective narrow band wavelength filter (of four filters) positioned above each of the pixels of the disjoint subset of pixels, the wavelength range of each narrow band wavelength filter falling within the broad wavelength spectrum of the point light source, the wavelength ranges of the narrow band wavelength filters being non-overlapping. The simulated results are then compared with a reference image based on a non-iterative approach, being a single-wavelength image reconstruction.

Under normal operating conditions of the snapshot approach, all four wavelengths are illuminating the object (and the sensor) at the same time. The filters on top of the sensor select only one narrow wavelength range for each pixel, which can be considered to record only one wavelength (or narrow wavelength range). To simulate this, a traditional sequential recording was performed, whereby the full sensor was illuminated sequentially with the four wavelengths hence resulting in four full resolution recordings (FIG. 7A).

Figures 7A, 7B, 7C, 7D:
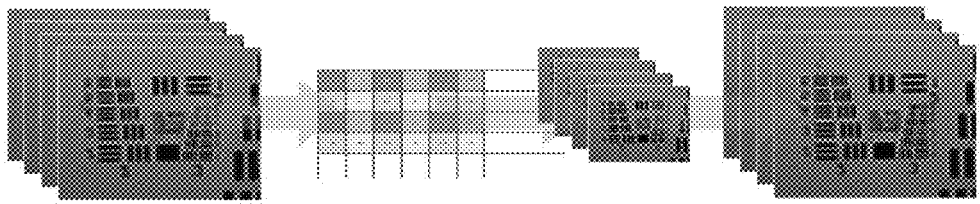
FIG. 7A is a schematic illustration of simulation results, according to example embodiments.
FIG. 7B is a schematic illustration of simulation results, according to example embodiments.
FIG. 7C is a schematic illustration of simulation results, according to example embodiments.
FIG. 7D is a schematic illustration of simulation results, according to example embodiments.

Then, the behavior of the snapshot sensor was simulated by subsampling these full resolution images the way the wavelength filters are to be organized on the sensor (see e.g. FIG. 7B). As a result, four low(er) resolution images are generated (FIG. 7C). The processed snapshot sensor would acquire one image at a time. It is straight forward to then separate this single image into a (similar) subset of four low(er) resolution images.

Figures 8A, 8B:
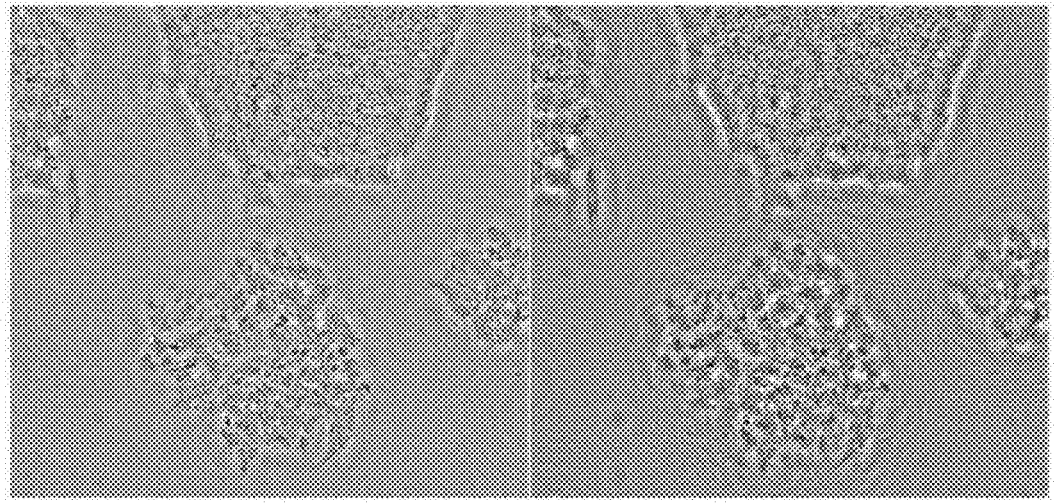
FIG. 8A shows a simulated snapshot image, according to example embodiments.
FIG. 8B shows a single wavelength reference, allowing an assessment of output resolution and image quality of methods, according to example embodiments.

To compare the outcome of this approach, an image interpolation step to go back to the original resolution of the input images was performed (FIG. 7D). This is to be able to compare the obtained quality and resolution of the snapshot approach versus the sequential approach. A normal multi-wavelength iterative reconstruction process was done. A comparison of the results is depicted in FIGS. 8A and 8B. Indeed, if high speed imaging is desired, then the resulting quality and resolution should best be compared with a single-wavelength (non-iterative) reconstruction.

It is clear that the resulting image quality is much better with the (simulated) snapshot approach (FIG. 8A) when compared to the non-iterative approach (FIG. 8B). This is at least due to the inherent twin-image distortion of the single wavelength reconstruction. With the (simulated) snapshot approach, an iterative reconstruction is still possible, which clearly results in a suppression of the inherent twin-image distortion.

In other embodiments, the present disclosure relates to a lens-free imaging device for imaging a moving sample. The lens-free imaging device comprises a radiation source and a line scanner.

The radiation source is adapted for emitting a set of at least two different wavelengths, e.g. at least three different wavelengths, towards the moving sample. The line scanner is adapted for obtaining a line scan per wavelength emitted by the radiation source and reflected by, scattered by and/or transmitted through the moving sample. The line scanner is also adapted for regularly obtaining a line scan per wavelength.

In some embodiments, either the radiation source or the line scanner is adapted for isolating the at least two different wavelengths.

The line scanner may in some embodiments be implemented as a linear photodetector array, e.g. one dimensional, and a plurality of linear detectors may be used or a single photodetector array, e.g. one dimensional, may be used in a time sharing mode. In other embodiments, the line scanner may be implemented as a two-dimensional photodetector array that is arranged to have certain sub-areas illuminated by different wavelength of the radiation source.

The radiation source can be a light source with wavelengths ranging between 450 nm and 1000 nm (e.g., between 530 nm and 700 nm). The latter range is suitable for blood cell imaging. In some embodiments, the spacing between the wavelengths of one set is smaller than 20 nm, for example smaller than 10 nm (e.g. between 5 and 10 nm). The spacing between the wavelengths of one set may even go down to 1 nm. The minimum wavelength difference is thereby determined by the full width half maximum (FWHM) of the emission spectrum of the radiation source. Such a set of wavelengths with a limited spacing between them may provide improved signal to noise ratio of the obtained image of the moving sample. The spacing between the wavelengths within a set of wavelengths may be selected such that the spectral response of the sample is not differing significantly between the different wavelengths within one set. The change between the line scans per wavelength caused by the change in spectral response may for example not be measurable. The sample may for example comprise fluorescent dyes or labels. In that case the spectral response on 5 nm to 10 nm spaced wavelengths is not differing significantly. In terms of the present disclosure, the change in spectral response of the sample on the different wavelength is limited if it is possible to apply phase recovery on the obtained line scans. Depending on the sample, this may sometimes be possible using wavelengths that are further separated that 10 nm, for example 20 nm, for example wavelengths of 640, 660, and 680 nm. If the wavelengths within one set are too much separated, phase recovery is not possible anymore because the spectral features of the sample under study are differing too much.

The pixels of the detector line can be panchromatic pixels. In some embodiments, the pixels of the detector line are hyperspectral sensors. In some embodiments, the detector line can be a line of pixels.

Lens-free imaging devices according to example embodiments may include a processor for stitching the obtain line scans to obtain an image of the sample. Thereby the line scans per wavelength are stitched together.

Lens-free imaging devices according to example embodiments may make it possible to do multi-wavelength imaging of a moving sample because of the speed of the line scanner which is higher than the speed of a large field of view image sensor. The speed of the moving sample (e.g. the highest flow rate of a blood sample) is limited by the maximum speed of the line scanner. The only limitation thereby is that the line scanner is fast enough to image the fastest rate of the moving sample. The speed of the moving sample thereby refers to the speed of the sample relative to the lens-free imaging device. Thereby, it may be that the sample is moving in front of the imaging device or inversely that the imaging device is moving in front of the sample.

In some embodiments, the line scanner may be controlled by a processor in order to control the rate at which the line scans per wavelength are regularly obtained. The controller may thereby take into account the speed of the sample. The rate at which the line scans per wavelength are regularly obtained may be constant or may be dynamically adapted.

In some embodiments, the obtained line scans are stitched together to obtain an image of the sample. In some embodiments, the lens-free imaging device comprises a processor for stitching together the obtained line scans. The processor may be integrated in the lens-free imaging device or it may be separate. Stitching of the obtained line scans can be done in real-time or it can be done in a post-processing step.

Thus images corresponding with the moving sample can be obtained. In case of a sample which is moving at a slower rate, this could result in a stretched image. However, e.g. in case of a laminar flow rate, this could be compensated for by processing the obtained image or by adjusting the rate at which line scans are obtained. Also imperfections in the flow may be compensated for by processing or post-processing the obtained line scans.

Lens-free imaging devices can include a light source and an image sensor. In between both a sample can be placed. When operating such lens-free imaging devices this may lead to twin image artifacts. The reason therefore being that the image sensor is only detecting the intensity of the received light and not the phase of the received light. In order to suppress such twin image artifacts it may be useful to recover the phase. This can be done be shifting the distance between the light source and the image sensor up and down. However, this may include, for example, a piezo stage to do the movement.

In some embodiments, this is done by using a set of at least two different wavelengths and by recombining the obtained images to get a combined image. In some embodiments, the phase is recovered by applying iterative phase retrieval on the obtained line scans. The iterative algorithm corrects for the change in path length based on the spacing between the wavelengths in one set. Thus it is possible to iteratively recovering the complex signal. This allows recovery of the original sample shape without the twin image distortion.

The lens-free imaging device may comprise a set of at least two wavelengths or a set of at least three wavelengths (i.e. a triplet) per set to enhance the signal to noise ratio. With an increasing number of wavelengths per set (e.g. 4, 6, 8, 16) also the suppression of the twin image artifact is increasing at the cost of a more complex lens-free imaging device. In some embodiments, the number of wavelengths in one set is 3 or 4. In certain embodiments it may increase to 6. However, the sensitivity increase is most significant with 3 or 4 wavelengths per set.

In some embodiments, the lens-free imaging device has a processor which is adapted for counting the number of particles in the moving sample. This may for example allow to obtain the concentration of the particles in the sample. These particles can be particles present in a liquid flow such as for example a blood flow. It may for example be possible to quantify the number of cells in a blood flow (e.g. white blood cells, red blood cells, platelets). Lens-free imaging device according to the present disclosure may be used to estimate hemoglobin and hematocrit. In addition they may give the concentrations of white blood cells including 3-part or 5-part differential. They may be used to estimate the complete blood count (CBC) and/or the mean cell volume (MCV) of red blood cells. In another application lens-free imaging devices according to the present disclosure may be used to quantify the concentration of particles in a gas flow.

In some embodiments, the radiation source has a spectrum covering the set of different wavelengths. For isolating the at least two different wavelengths in a set the line scanner comprises a set of filters. Each filter adapted for filtering a wavelength and each filter positioned in front of a separate detector. The radiation source with a spectrum covering the different wavelengths can for example be a white diode.

Figure 9:
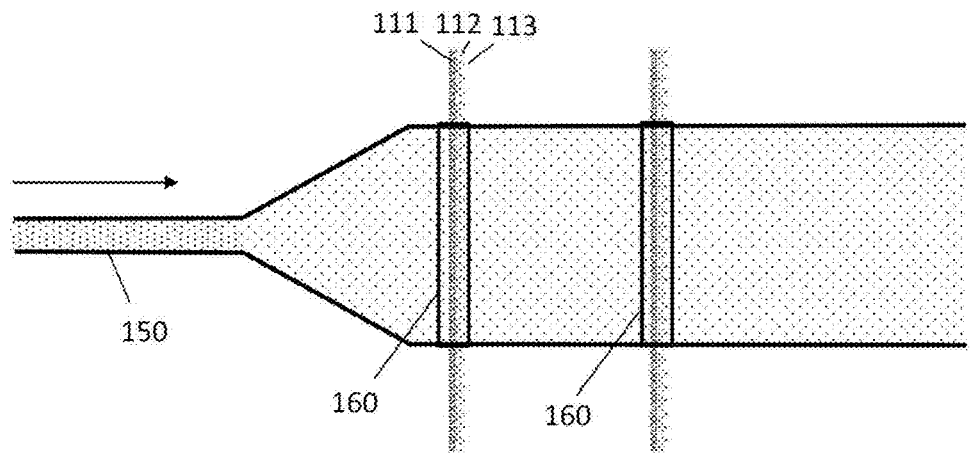
FIG. 9 shows a schematic drawing of the top view of a lens-free imaging device that includes a radiation source with a broad spectrum covering the set of different wavelengths, according to example embodiments.

FIG. 9 shows a schematic drawing of the top view of a lens-free imaging device 100 comprising a radiation source 110 with a broad spectrum covering the set of different wavelengths 111, 112, 113, in accordance with some embodiments. The sample is carried by the microfluidic device 150. The rectangular area 160 shows the detection area of the imaging device 100.

Figure 10:
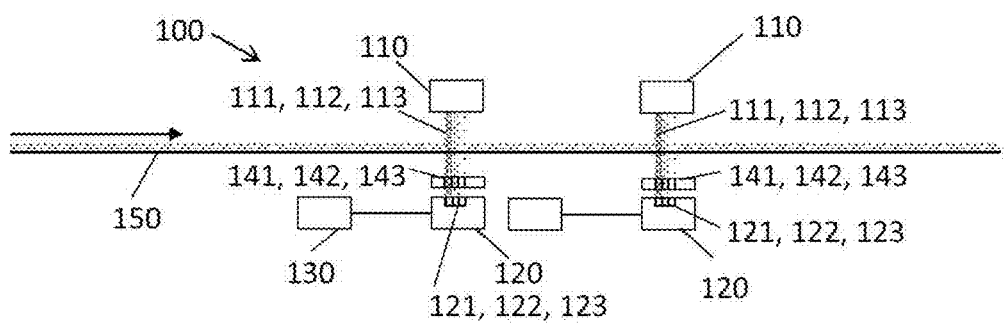
FIG. 10 shows a schematic drawing of the side view of the same lens-free imaging device as in FIG. 9, according to example embodiments.

FIG. 10 shows a schematic drawing of the side view of the same lens-free imaging device as in FIG. 9. FIG. 10 shows the radiation source 110. In this example the radiation source is emitting a radiation wavefront covering a set of three different wavelengths 111, 112, 113 through a sample carried by a microfluidic device 150. The radiation wavefront is filtered by a set of filters 141, 142, 143 to obtain separated radiation waves with wavelengths 111, 112, 113. Each radiation wave is detected by a separate detector line 121, 122, 123 of the line scanner 120. The processor 130 is adapted for stitching the obtained line scans per wavelength.

In some embodiments, the radiation source may include single wavelength illumination sources for emitting the different wavelengths of a set of wavelengths. Each illumination source may be positioned for only illuminating one corresponding detector line of the line scanner.

Figure 11:
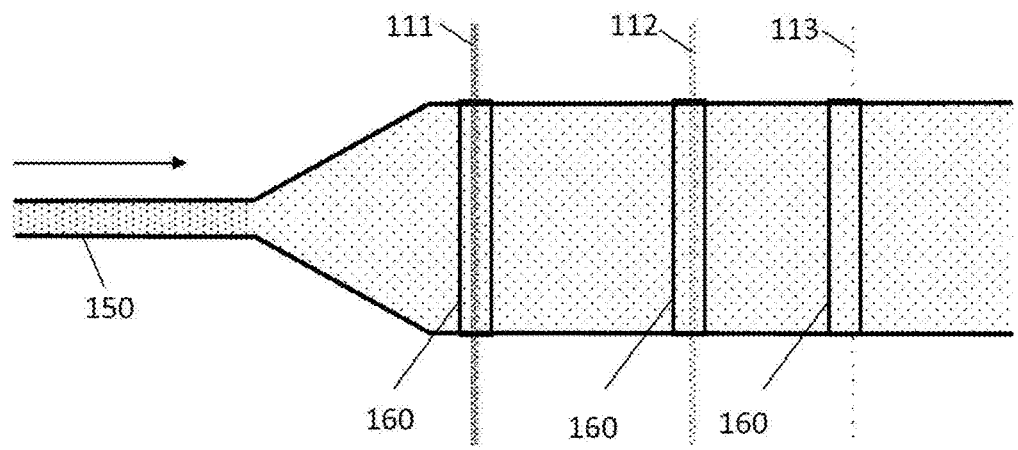
FIG. 11 shows a schematic drawing of the top view of a lens-free imaging device that includes a radiation source, which includes single wavelength illumination sources for emitting the set of different wavelengths, according to example embodiments.

FIG. 11 shows a schematic drawing of the top view of a lens-free imaging device 100 comprising a radiation source 110, comprising single wavelength illumination sources for emitting the set of different wavelengths 111, 112, 113, in accordance with example embodiments. The sample is carried by the microfluidic device 150. The rectangular areas 160 show the detection areas of the imaging device 100.

Figure 12:
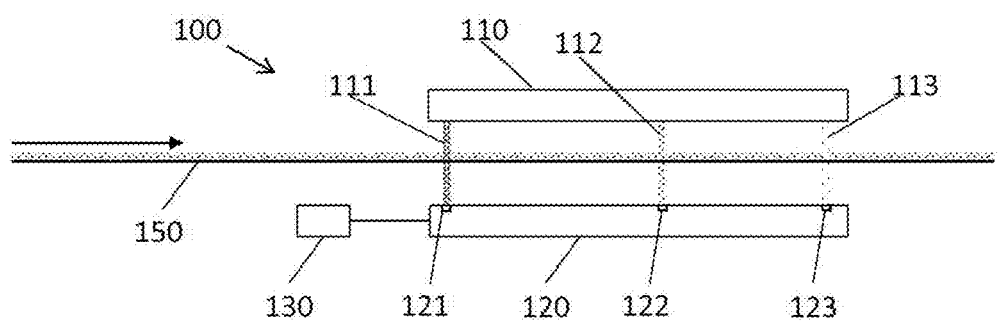
FIG. 12 shows a schematic drawing of the side view of the same lens-free imaging device as in FIG. 11, according to example embodiments.

FIG. 12 shows a schematic drawing of the side view of the same lens-free imaging device as in FIG. 11. FIG. 11 shows the radiation source 110. In this example the radiation source 110 comprises single wavelength illumination sources for emitting a set of three different wavelengths 111, 112, 113 through a sample carried by a microfluidic device 150. Each radiation wave is detected by a separate detector line 121, 122, 123 of the line scanner 120. The processor 130 is adapted for stitching the obtained line scans per wavelength.

Lens-free imaging devices according to the present disclosure may be designed for measuring different sets of wavelengths. The wavelength spacing between these sets may be so high that that the spectral response of the sample may be different for the different sets of wavelengths. It may for example be possible to distinguish types of cells/particles because of their different response on a different set of wavelengths.

In example embodiments, a set of three blue, a set of three red and a set of three green diodes are the radiation source. The diodes of each set have three different wavelengths and may provide multi-wavelength imaging on a moving sample. Thanks to the presence of a blue, of a red and of green set it is as well possible to do multi-spectral analysis of the moving sample.

In other example embodiments, the set of three blue, three red and three green diodes is replaced by a white LED. In this embodiment the distinction between the different wavelengths is made by filters. This may result in a less complex lens-free imaging device than in a case where three blue, three red, and three green diodes are used.

In the examples above triplets are used, however, this is not to be viewed as limiting. For example, in some embodiments, 4 or more separated wavelengths per set can be used. Also, for the examples above a set of red, a set of green, and a set of blue diodes are used, but this should also not be viewed as limiting. Depending on the application, an optimized set of spectral components can be selected.

In some embodiments, the present disclosure also relates to a method for imaging a moving sample. The method comprises emitting a set of at least two different wavelengths towards the moving sample wherein the spacing between the wavelengths is selected such that the spectral response of the sample is not varying for the different wavelengths within one set.

The method also comprises regularly obtaining a line scan per wavelength emitted by the radiation source and reflected by, scattered by and/or transmitted through the moving sample wherein the speed of obtaining the line scan per wavelength allows imaging of the moving sample. This is done while emitting a set of at least two different wavelengths.

The method also comprises stitching the obtained line scans per wavelength together thus obtaining an image per wavelength. This may be done in real-time while measuring or it may be done in a post-processing step.

The method also includes recombining the obtained images to get a combined image of the sample.

In some embodiments, the method includes analyzing the obtained combined image of the sample thereby counting the number of particles in the combined image.

What is claimed is:

1. A lens-free imaging device for imaging a moving sample, comprising:
    a radiation source configured to emit a set of at least two different wavelengths towards the moving sample, wherein the lens-free imaging device is configured to image samples for which a spectral response does not substantially vary for a set of at least two different wavelengths; and
    a line scanner configured to obtain a line scan per wavelength emitted by the radiation source and reflected by, scattered by, or transmitted through the moving sample, wherein the line scanner is configured to regularly obtain a line scan per wavelength, and
    wherein either the radiation source or the line scanner is configured to isolate data of the at least two different wavelengths.

2. The lens-free imaging device according to claim 1, further comprising:
    a processor programmed to stitch the obtained line scans per wavelength to obtain, for each wavelength, an image of the sample.

3. The lens-free imaging device according to claim 2, wherein the processor is further programmed to recombine a plurality of images of the sample to obtain a combined image.

4. The lens-free imaging device according to claim 3, wherein the processor is further programmed to analyze the combined image to count a number of particles in the moving sample.

5. The lens-free imaging device according to claim 1,
    wherein the radiation source has a spectrum covering the set of at least two different wavelengths,
    wherein the line scanner comprises a filter for each wavelength in the set of at least two different wavelengths, and
    wherein each filter is disposed in front of a separate detector line of the line scanner.

6. The lens-free imaging device according to claim 1, wherein the radiation source comprises at least two single-wavelength illumination sources, each positioned to illuminate a single corresponding detector line of the line scanner.

7. The lens-free imaging device according to claim 1,
    wherein the radiation source is configured to transmit at least two sets of wavelengths,
    wherein a spacing between the two sets of wavelengths is greater than a spacing of wavelengths within either set, and
    wherein either the radiation source or the line scanner is configured to isolate the at least two different wavelengths within each set.

8. The lens-free imaging device according to claim 1, further comprising a microfluidic device configured to carry a sample flow such that the sample flow can be imaged by the radiation source and the line scanner, wherein, when the sample flow is flowing in the microfluidic device, a flow speed of the sample flow is smaller than or equal to a speed able to be imaged by the line scanner.

9. The lens-free imaging device according to claim 1, wherein the lens-free imaging device is configured to perform industrial inspection.

10. A method for imaging a moving sample, the method comprising:
    emitting, by a radiation source, a set of at least two different wavelengths towards the moving sample, wherein a spacing between the at least two wavelengths is selected such that a spectral response of the moving sample is not varying for the at least two wavelengths within the set of at least two different wavelengths,
    regularly obtaining a line scan per wavelength emitted by the radiation source and reflected by, scattered by, or transmitted through the moving sample, wherein a speed of obtaining the line scan per wavelength allows an imaging of the moving sample, stitching the obtained line scans per wavelength together to obtain an image per each wavelength in the set of at least two different wavelengths, recombining the obtained images to obtain a combined image of the moving sample.

11. The method according to claim 10, further comprising analyzing the combined image of the moving sample to count a number of particles in the combined image.

12. A diagnostic device for diagnosing a status of an object or a patient, the diagnostic device comprising:

a lens-free imaging device for imaging a moving sample, comprising:

a radiation source configured to emit a set of at least two different wavelengths towards the moving sample, wherein the lens-free imaging device is configured to image samples for which a spectral response does not substantially vary for a set of at least two different wavelengths; and a line scanner configured to obtain a line scan per wavelength emitted by the radiation source and reflected by, scattered by, or transmitted through the moving sample, wherein the line scanner is configured to regularly obtain a line scan per wavelength, wherein either the radiation source or the line scanner is configured to isolate data of the at least two different wavelengths, and wherein the lens-free imaging device is used to determine a quality or quantity of particles in a flow of a sample of the object or of the patient; and an output device for providing an output of the lens-free imaging device on which a diagnosis can be based.

13. The diagnostic device according to claim 12, wherein the output device is configured to output a number of cells in a blood flow.

14. The diagnostic device according to claim 12, wherein the lens-free imaging device further comprises a processor programmed to stitch the obtained line scans per wavelength to obtain, for each wavelength, an image of the sample.

15. The diagnostic device according to claim 14, wherein the processor is further programmed to recombine a plurality of images of the sample to obtain a combined image.

16. The diagnostic device according to claim 15, wherein the processor is further programmed to analyze the combined image to count a number of particles in the moving sample.

17. The diagnostic device according to claim 12, wherein the radiation source has a spectrum covering the set of at least two different wavelengths, wherein the line scanner comprises a filter for each wavelength in the set of at least two different wavelengths, and wherein each filter is disposed in front of a separate detector line of the line scanner.

18. The diagnostic device according to claim 12, wherein the radiation source comprises at least two single-wavelength illumination sources, each positioned to illuminate a single corresponding detector line of the line scanner.

19. The diagnostic device according to claim 12, wherein the radiation source is configured to transmit at least two sets of wavelengths, wherein a spacing between the two sets of wavelengths is greater than a spacing of wavelengths within either set, and wherein either the radiation source or the line scanner is configured to isolate the at least two different wavelengths within each set.

20. The diagnostic device according to claim 12, wherein the lens-free imaging device further comprises a microfluidic device configured to carry a sample flow such that the sample flow can be imaged by the radiation source and the line scanner, wherein, when the sample flow is flowing in the microfluidic device, a flow speed of the sample flow is smaller than or equal to a speed able to be imaged by the line scanner.

* * * * *